(12) United States Patent
Hoffman et al.

(10) Patent No.: US 8,483,352 B2
(45) Date of Patent: Jul. 9, 2013

(54) STACKED X-RAY DETECTOR ASSEMBLY AND METHOD OF MAKING SAME

(75) Inventors: David Michael Hoffman, New Berlin, WI (US); Jeffrey Alan Kautzer, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 281 days.

(21) Appl. No.: 12/967,093

(22) Filed: Dec. 14, 2010

(65) Prior Publication Data

US 2011/0080993 A1 Apr. 7, 2011

Related U.S. Application Data

(63) Continuation-in-part of application No. 11/523,359, filed on Sep. 19, 2006, now Pat. No. 7,974,377.

(51) Int. Cl.
*A61B 6/03* (2006.01)

(52) U.S. Cl.
USPC ............................................. 378/19; 378/98.8

(58) Field of Classification Search
USPC ............................ 378/4–20, 98.8; 250/370.09
See application file for complete search history.

(56) References Cited

U.S. PATENT DOCUMENTS

| 4,709,382 | A | * | 11/1987 | Sones ............................... 378/62 |
| 5,223,717 | A | | 6/1993 | Charpak |
| 6,041,097 | A | | 3/2000 | Roos et al. |
| 6,421,412 | B1 | | 7/2002 | Hsieh et al. |
| 7,016,455 | B2 | | 3/2006 | Bruder et al. |
| 7,019,303 | B2 | | 3/2006 | Homme et al. |
| 7,039,153 | B2 | | 5/2006 | Bruder et al. |
| 7,356,115 | B2 | | 4/2008 | Ford et al. |
| 7,426,260 | B2 | | 9/2008 | Cantu et al. |
| 2003/0002626 | A1 | * | 1/2003 | Hoheisel et al. ............. 378/98.8 |
| 2003/0123718 | A1 | | 7/2003 | Edic et al. |
| 2004/0109532 | A1 | | 6/2004 | Ford et al. |
| 2006/0086905 | A1 | | 4/2006 | Fritzler et al. |
| 2010/0150305 | A1 | | 6/2010 | Nowak et al. |

\* cited by examiner

*Primary Examiner* — Hoon Song (74) *Attorney, Agent, or Firm* — Ziolkowski Patent Solutions Group, SC (57) ABSTRACT

An x-ray detector assembly includes a curvilinear detector assembly that has a first side section that includes a first plurality of detector modules, a second side section that includes a second plurality of detector modules, and a third section that includes a third plurality of detector modules. The third section is positioned between the first and second side sections in a channel direction. The x-ray detector assembly also includes a first flat panel digital projection detector and a first detector mounting structure that is configured to align the first flat panel digital projection detector in a first position to block the third section of the curvilinear detector assembly from receiving x-rays emitting from an x-ray source toward the curvilinear detector assembly in the x-ray penetration direction.

21 Claims, 9 Drawing Sheets

STACKED X-RAY DETECTOR ASSEMBLY AND METHOD OF MAKING SAME

CROSS-REFERENCE TO RELATED APPLICATION

The present application is a continuation-in-part of, and claims priority to, U.S. non-provisional application Ser. No. 11/523,359, filed Sep. 19, 2006, the disclosure of which is incorporated herein by reference.

BACKGROUND OF THE INVENTION

Embodiments of the invention relate generally to diagnostic imaging methods and apparatus, and more particularly, to an apparatus and method of manufacturing a stacked x-ray detector assembly.

Typically, in CT imaging systems, an x-ray source emits a fan-shaped beam toward a subject or object, such as a patient or a piece of luggage. Hereinafter, the terms "subject" and "object" shall include anything capable of being imaged. Generally, the x-ray source and the detector assembly are rotated about the gantry within an imaging plane and around the subject. X-ray sources typically include x-ray tubes, which emit the x-ray beam at a focal point. The beam, after being attenuated by the subject, impinges upon an array of radiation detectors.

The detector assembly is typically made of a plurality of detector modules. Data representing the intensity of the received x-ray beam at each of the detector elements is collected across a range of gantry angles. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis that ultimately produces an image.

Conventional CT systems emit an x-ray with a polychromatic spectrum. The x-ray attenuation of each material in the subject depends on the energy of the emitted x-ray. If CT projection data is acquired at multiple x-ray energy levels or spectra, the data contains additional information about the subject or object being imaged that is not contained within a conventional CT image. For example, spectral CT data can be used to produce a new image with x-ray attenuation coefficients equivalent to a chosen monochromatic energy. Such a monochromatic image includes image data where the intensity values of the voxels are assigned as if a CT image were created by collecting projection data from the subject with a monochromatic x-ray beam. Spectral CT data facilitates better discrimination of tissues, making it easier to differentiate between materials such as tissues containing calcium and iodine, for example.

A principle objective of energy sensitive scanning is to obtain diagnostic CT images that enhance information (contrast separation, material specificity, etc.) within the image by utilizing two or more scans at different chromatic energy states. High frequency generators have made it possible to switch the kVp potential of the high frequency electromagnetic energy projection source on alternating views. As a result, data for two or more energy sensitive scans may be obtained in a temporally interleaved fashion rather than two separate scans made several seconds apart as typically occurs with previous CT technology. The interleaved projection data may furthermore be registered so that the same path lengths are defined at each energy level using, for example, some form of interpolation.

Conventional curvilinear detector array include a large number of individual detector elements arranged on the detector array. The detector elements are scintillator/photodiode cells arranged in two-dimensional modules that are then combined into two-dimensional detector area arrays. The coverage area of the detector array is defined by the number of detector elements in each 2D module and the number of 2D modules that are combined to form the detector assembly.

While known systems and methods that include conventional curvilinear detector arrays can be employed to acquire projection data at multiple x-ray energy levels or spectra and display, the coverage area of a scan is defined by the size of the detector array. Because each individual detector element has its own element-specific readout channel, the larger the detector assembly the more costly and complex the imaging system becomes.

For various imaging applications, such as cardiac scanning, it would be advantageous to acquire all of the image data for the object being imaged in a single rotation of the gantry. Such an image data acquisition technique has a number of benefits, including minimizing motion artifacts, as an example. However, the coverage area of the detector assembly must be sized based on the size of the projection of the object being imaged on the detector array. A curvilinear detector assembly designed with a large enough coverage area to image a heart, for example, would be extremely complex and cost prohibitive.

Therefore, it would be desirable to design an x-ray detector assembly that overcomes the aforementioned drawbacks.

BRIEF DESCRIPTION OF THE INVENTION

In accordance with one aspect of the invention, an x-ray detector assembly includes a curvilinear detector assembly that has a first side section that includes a first plurality of detector modules, a second side section that includes a second plurality of detector modules, and a third section that includes a third plurality of detector modules. The third section is positioned between the first and second side sections in a channel direction. The x-ray detector assembly also includes a first flat panel digital projection detector and a first detector mounting structure that is configured to align the first flat panel digital projection detector in a first position to block the third section of the curvilinear detector assembly from receiving x-rays emitting from an x-ray source toward the curvilinear detector assembly in the x-ray penetration direction.

In accordance with another aspect of the invention, a method of manufacturing a detector assembly includes the step of providing a curvilinear detector array comprising a plurality of detectors arranged therein, the curvilinear detector array having a length defined in a channel direction between a first side and a second side of the curvilinear detector array and a width defined in a slice direction between a third side and a fourth side of the curvilinear detector array. The method also includes the step of providing a first flat panel detector comprising a top surface configured to face an x-ray source, the top surface having a width defined in the slice direction between a first edge of the top surface and a second edge of the top surface opposite the first edge, wherein the width of the first flat panel detector is greater than the width of the curvilinear detector array. Further, the method includes the step of coupling the first flat panel detector to a first detector mounting assembly having an obstructing position configured to align the first flat panel detector above the curvilinear detector array in an x-ray penetration direction such that the first flat panel detector is substantially aligned with a central portion of the curvilinear detector array in the slice and channel directions.

In accordance with another aspect of the invention, a CT system includes a rotatable gantry having an opening therein for receiving an object to be scanned, a table positioned within the opening of the rotatable gantry and moveable through the opening in a z-direction, and an x-ray source coupled to the rotatable gantry and configured to project a beam of x-rays toward the object to be scanned. The CT system also includes a detector assembly positioned to receive the beam of x-rays from the x-ray source. The detector assembly includes a curvilinear detector assembly having a plurality of detectors and a first flat panel digital detector arranged between a central portion of the curvilinear detector assembly and the x-ray source such that a first plurality of x-rays projecting from the x-ray source toward the central portion of the curvilinear detector assembly are absorbed by the first flat panel digital detector.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy.

The invention will be described with respect to a "third generation" CT scanner, but is equally applicable with other CT systems.

In addition, certain embodiments of the present invention provide systems, methods, and computer instructions for acquiring multi-energy data, such as dual energy data, for example. Certain multi-energy data can be used in spectral imaging systems, such as photon counting systems, for example. Dual energy data, which is a type of multi-energy data, can be embodied in monochromatic images, material density images, and/or effective-Z images. While many of the embodiments described herein are discussed in connection with dual energy data, the embodiments are not limited to dual energy data and can be used in connection with other types of multi-energy data, as one skilled in the art will appreciate.

Figure 1:
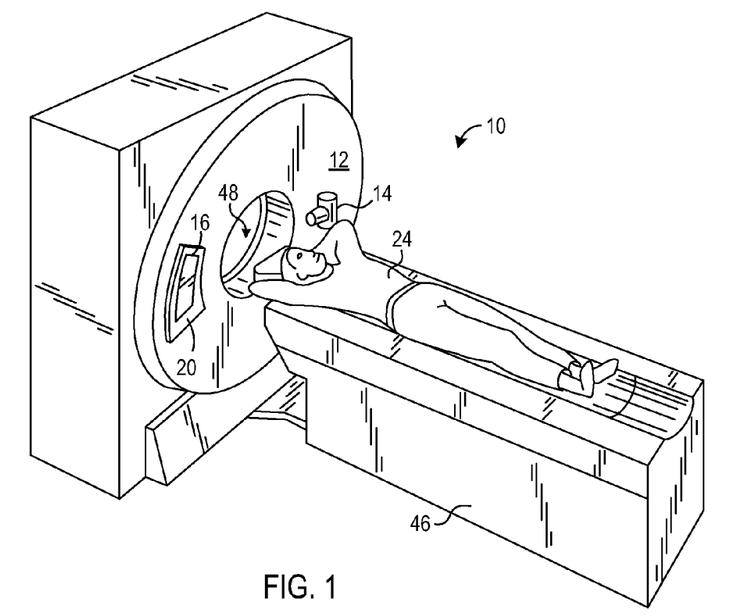
FIG. 1 is a pictorial view of a CT imaging system.
Figure 2:
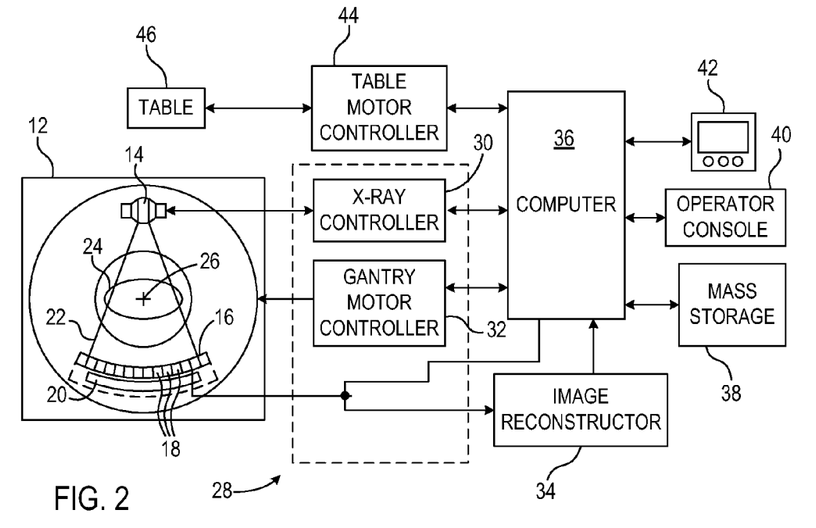
FIG. 2 is a block schematic diagram of the system illustrated in FIG. 1.

Referring to FIG. 1, a CT imaging system 10 is shown as including a gantry 12 representative of a "third generation" CT scanner. Gantry 12 has an x-ray source 14 that projects a beam of x-rays toward a detector assembly or collimator 16 on the opposite side of the gantry 12. Referring now to FIG. 2, detector assembly 16 is formed by a plurality of detectors or detector modules 18 and data acquisition systems (DAS) 20. The plurality of detectors 18 sense the projected x-rays 22 that pass through a medical patient 24, and DAS 20 converts the data to digital signals for subsequent processing. Each detector 18 produces an analog electrical signal that represents the intensity of an impinging x-ray beam and hence the attenuated beam as it passes through the patient 24. During a scan to acquire x-ray projection data, gantry 12 and the components mounted thereon rotate about a center of rotation 26.

Rotation of gantry 12 and the operation of x-ray source 14 are governed by a control mechanism 28 of CT system 10. Control mechanism 28 includes an x-ray controller 30 that provides power and timing signals to an x-ray source 14 and a gantry motor controller 32 that controls the rotational speed and position of gantry 12. An image reconstructor 34 receives sampled and digitized x-ray data from DAS 20 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 20, x-ray controller 30 and gantry motor controller 32. In addition, computer 36 operates a table motor controller 44 which controls a motorized table 46 to position patient 24 and gantry 12. Particularly, table 46 moves patients 24 through a gantry opening 48 of FIG. 1 in whole or in part.

Figure 3:
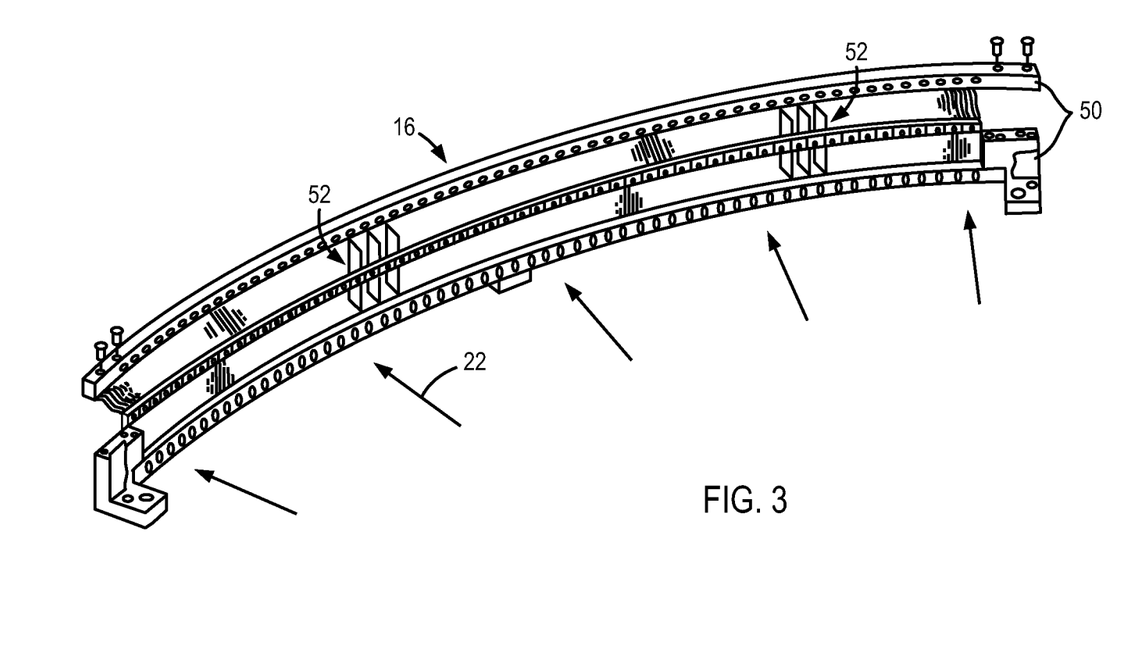
FIG. 3 is a perspective view of one embodiment of a CT system detector array.

As shown in FIG. 3, detector assembly 16 includes rails 50 having collimating blades or plates 52 placed therebetween. Plates 52 are positioned to collimate x-rays 22 before such beams impinge upon, for instance, detector 18 of FIG. 4 positioned on detector assembly 16. In one embodiment, detector assembly 16 includes 57 detectors 18, each detector 18 having an array size of 64×16 of pixel elements 54. As a result, detector assembly 16 has 64 rows and 912 columns (16×57 detectors) which allows 64 simultaneous slices of data to be collected with each rotation of gantry 12.

Figure 4:
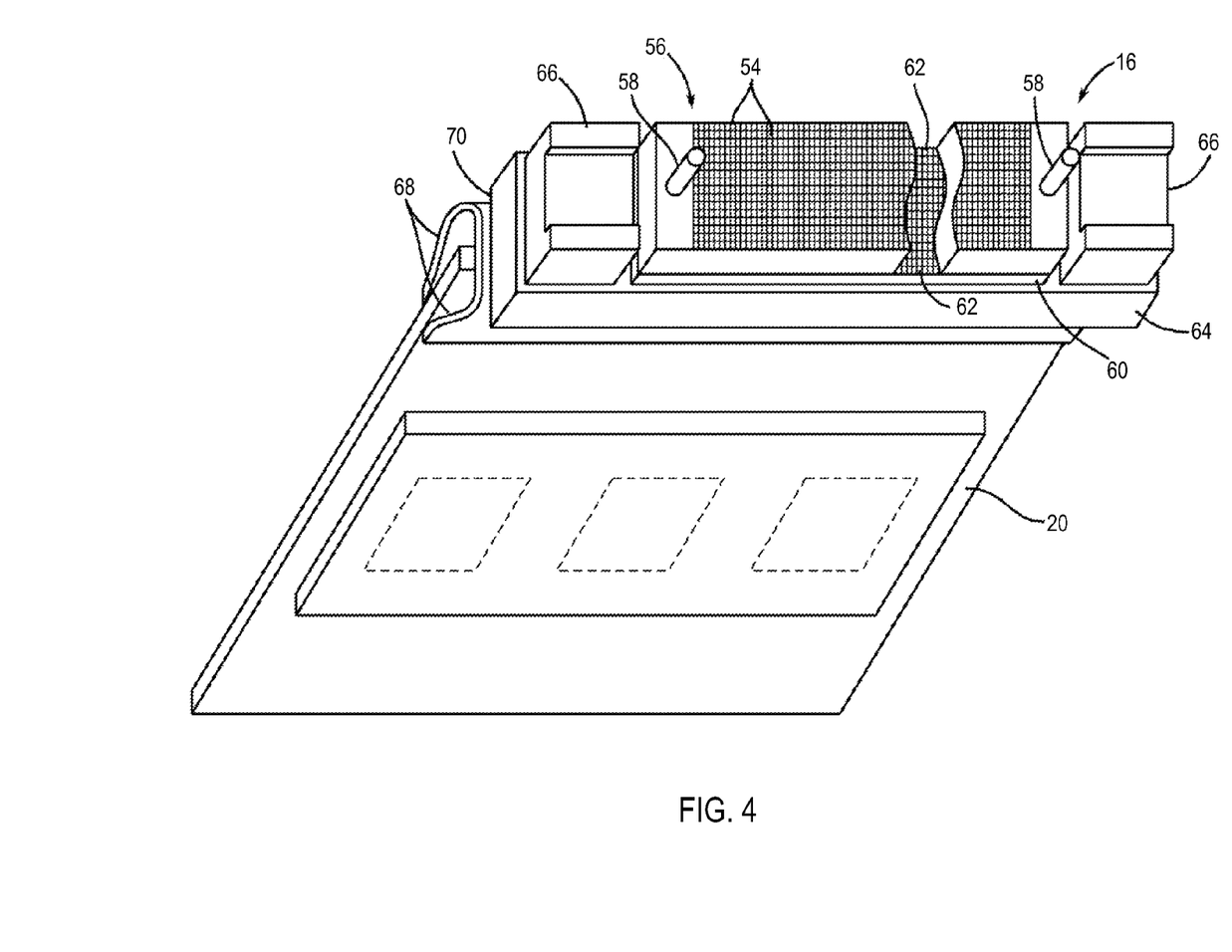
FIG. 4 is a perspective view of one embodiment of a detector.

Referring to FIG. 4, detector 18 includes DAS 20, with each detector 18 including a number of detector elements 54 arranged in pack 56. Detectors 18 include pins 58 positioned within pack 56 relative to detector elements 54. Pack 56 is positioned on a backlit diode array 60 having a plurality of diodes 62. Backlit diode array 60 is in turn positioned on multi-layer substrate 64. Spacers 66 are positioned on multi-layer substrate 64. Detector elements 54 are optically coupled to backlit diode array 60, and backlit diode array 60 is in turn electrically coupled to multi-layer substrate 64. Flex circuits 68 are attached to face 70 of multi-layer substrate 64 and to DAS 20. Detectors 18 are positioned within detector assembly 16 by use of pins 58.

In the operation of one embodiment, x-rays impinging within detector elements 54 generate photons which traverse pack 56, thereby generating an analog signal which is detected on a diode within backlit diode array 60. The analog signal generated is carried through multi-layer substrate 64, through flex circuits 68, to DAS 20 wherein the analog signal is converted to a digital signal.

Figure 5:
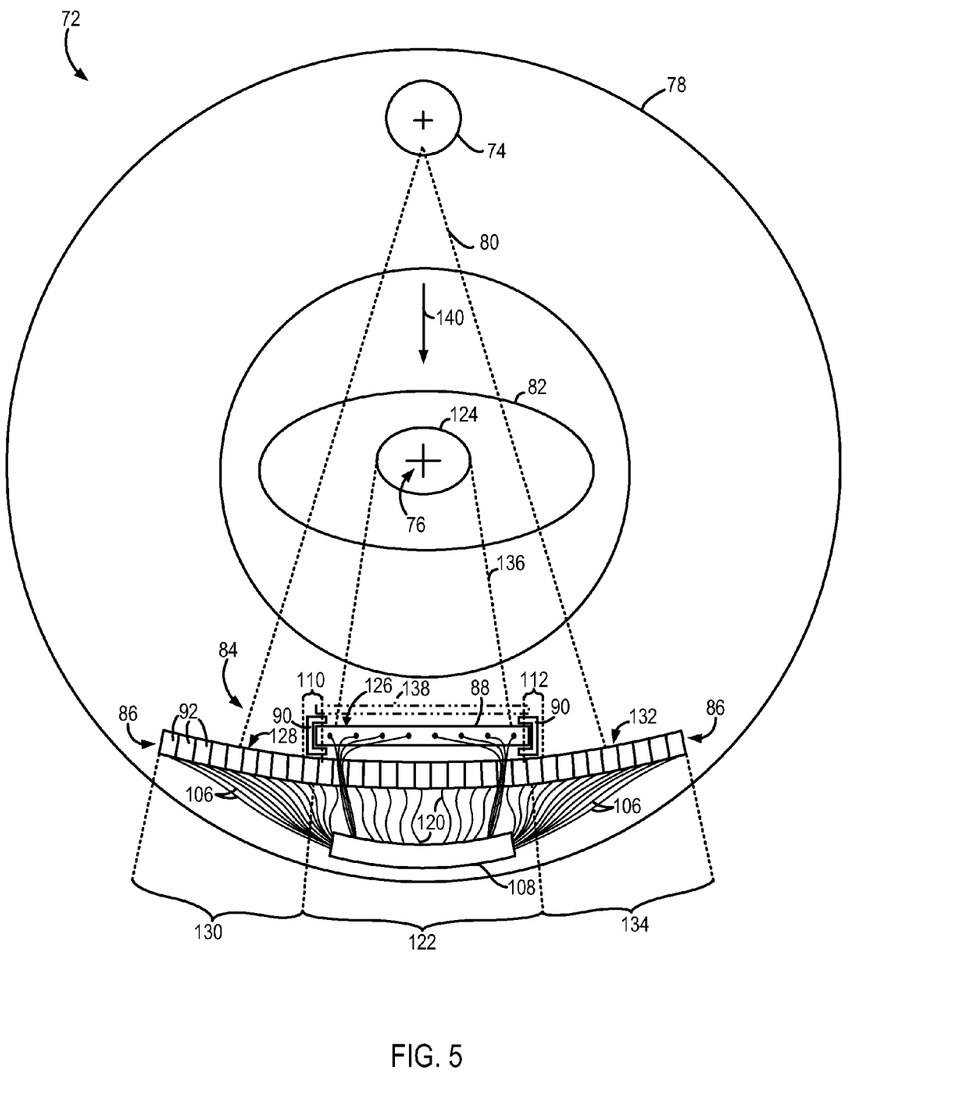
FIG. 5 is a cross-sectional view of a detector assembly in accordance with an embodiment of the invention.

FIG. 5 illustrates a side view diagram of a portion of an imaging system 72, such as, for example, CT imaging system 10 of FIG. 1. Imaging system 72 includes an x-ray source 74 that is configured to rotate about a center of rotation 76 of a rotatable gantry 78. A beam of x-rays 80 is produced when high-speed electrons emitted from x-ray source 74 impact the surface of a target portion (not shown) of x-ray source 74. Beam of x-rays 80 passes through a patient 82 and impinges upon a detector assembly 84.

Referring now to FIGS. 5-9, detector assembly 84 includes a curvilinear detector assembly or array 86 and a flat panel digital projection radiographic detector 88 coupled to a mounting bracket 90. Curvilinear detector assembly 86, includes a plurality of individual detectors 92 each having a number of detector elements (not shown), similar to detector elements 54 of detector 18 (FIG. 4). In one embodiment, each detector 92 has a width of approximately 16 mm, measured in the x-direction (channel direction) 94, and a height of approximately 64 mm, measured in the z-direction (slice direction) 96. Curvilinear detector assembly 86 has a length defined in the x-direction 94 between a first side 98 and a second side 100 and a width defined in the z-direction 96 between a third side 102 and a fourth side 104.

A readout channel 106 transmits electrical signals for each detector 92 from a respective detector 92 to a data acquisition system 108. Data acquisition system 108 converts the data to digital signals. The digital signals are transmitted to an image reconstructor, such as image reconstructor 34 (FIG. 2) for reconstruction, which may apply advanced calibration and corrections to account for interference at the transition regions 110, 112 between flat panel digital detector 88 and curvilinear detector assembly 86.

Figure 6:
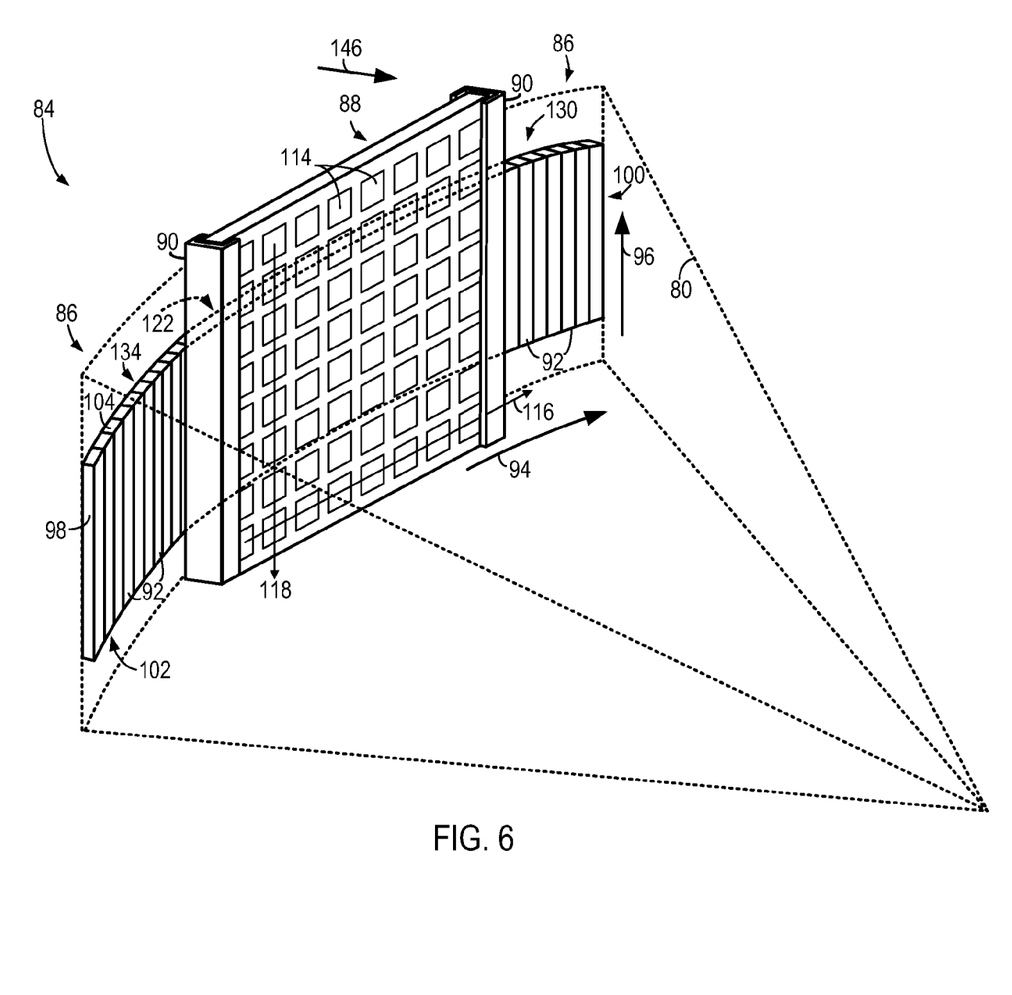
FIG. 6 is a perspective view of the detector assembly of FIG. 5 in accordance with an embodiment of the invention.

Flat panel detector 88 is a solid state digital projection radiographic detector such as a digital fluoroscopy panel typically used for catheter imaging. Flat panel detector 88 that includes an array of pixels 114 arranged in rows and columns. Unlike a conventional curvilinear detector assembly, such as detector assembly 86, pixels 114 of flat panel detector 88 are associated with a matrix of scan lines 116 and read lines 118, as shown in FIG. 6. Flat panel detector 88 includes a single readout channel 120 per read line 118. In one embodiment, flat panel detector 88 is a Revolution™ XR/d detector commercially available from the GE Healthcare business of General Electric Company.

Detector assembly 84 is aligned with x-ray source 74 such that beam of x-rays 80 passes through medical patient 82 and impinges upon flat panel detector 88 and curvilinear detector assembly 86. As shown in FIG. 5, flat panel detector 88 is positioned above a center portion 122 of curvilinear detector assembly 86 and is aligned with a region of interest 124 of patient 82. Thus, after passing through patient 82, beam of x-rays 80 impinges upon a top surface 126 of flat panel detector 88, a top surface 128 of a first side portion 130 of curvilinear detector assembly 86, and a top surface 132 of a second side portion 134 curvilinear detector assembly 86. Flat panel detector 88 is sized such that a full projection 136 of region of interest 124 impinges upon flat panel detector 88. Thus, flat panel detector 88 may be the size of a projected organ of interest, such as a heart, liver, or lung according to various embodiments. In one embodiment, flat panel detector 88 has a coverage area of approximately 20 cm by 20 cm measured in the x- and z-directions 94, 96. Optionally, a flat panel collimator assembly or grid 138 (shown in phantom) may be positioned in front of flat panel detector 88 in an x-ray penetration direction 140 for collimating x-ray beams received at flat panel detector 88.

The coverage area of flat panel detector 88 is at least equal to the size of the projection 136 of region of interest 124 to ensure that x-rays traveling in an x-ray penetration direction 140 and passing through region of interest 124 impinge upon flat panel detector 88. Thus, the portion of beam of x-rays 80 that impinges upon on curvilinear detector assembly 86 corresponds to regions of patient 82 outside region of interest 124.

According to various embodiments, region of interest 124 corresponds to an organ being imaged, such as a heart, lung, or liver as examples. Thus, for a cardiac scanning application where the region of interest 124 is defined as the heart, a whole heart of an adult may be scanned during a single rotation of rotatable gantry 78, since the coverage area of flat panel detector 88 is larger than the projection 136 of the heart on flat panel detector 88.

In one embodiment, mounting bracket 90 is a fixed bracket mounted within rotatable gantry 78 such that flat panel detector 88 is substantially centered above center portion 122 of curvilinear detector assembly 86 in the x-ray penetration direction 140. Alternatively, mounting bracket 90 comprises a pair of moveable guide rails that allow flat panel detector 88 to be moved into and out of alignment with curvilinear detector assembly 86, as described in detail with respect to FIGS. 7 and 8.

Figure 7:
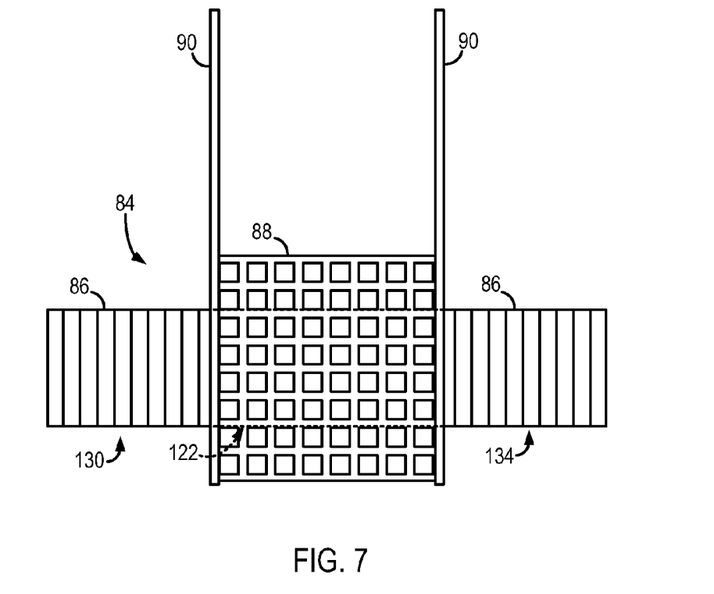
FIG. 7 is a block schematic diagram of the detector assembly of FIG. 5 illustrating a flat panel detector in a first position.
Figure 8:
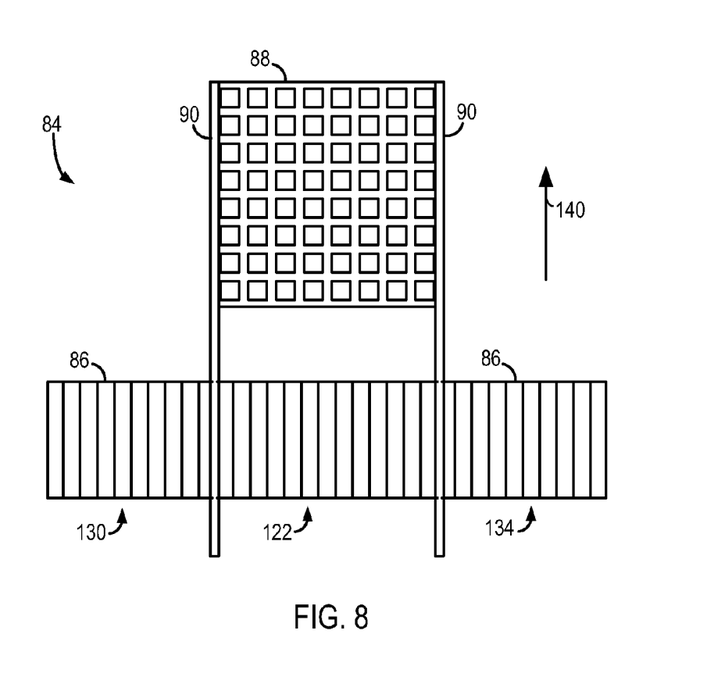
FIG. 8 is another block schematic diagram of the detector assembly of FIG. 5 illustrating the flat panel detector in a second position.

FIG. 7 is a block schematic diagram of flat panel detector 88 in a first position, wherein flat panel detector 88 is positioned above and substantially overlaps center portion 122 of curvilinear detector assembly 86. FIG. 8 is a block schematic diagram of detector assembly 84 with flat panel detector 88 in a second position, wherein flat panel detector 88 is offset from flat panel detector 88 in the z-direction 96. When flat panel detector 88 is in the first position (FIG. 7), x-rays 80 directed toward detector assembly 86 in the x-ray penetration direction 140 impinge flat panel detector 88; when flat panel detector 88 is in the second position (FIG. 8), x-rays 80 directed toward detector assembly 86 impinge center portion 122 of curvilinear detector assembly 86.

Figure 9:
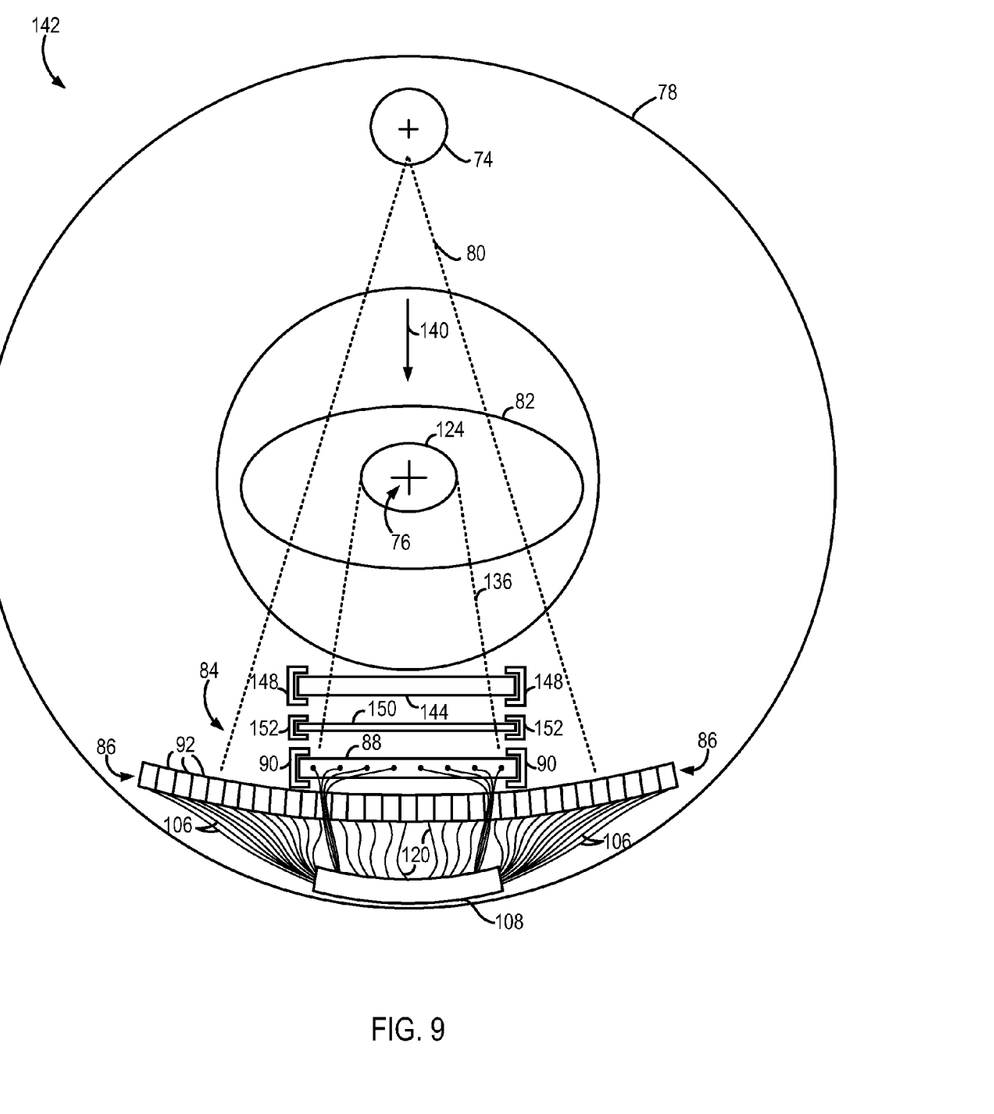
FIG. 9 is a cross-sectional view of a detector assembly in accordance with another embodiment of the invention.

Referring now to FIG. 9, an imaging system 142 is shown according to an alternative embodiment. Imaging system 142 is configured in a similar manner as described with respect to imaging system 72 of FIG. 5 in that imaging system 142 includes x-ray source 74 positioned to direct beam of x-rays 80 toward detector assembly 84, which includes a flat panel detector 88 positioned above a curvilinear detector assembly 86. Flat panel detector 88 is mounted on mounting bracket 90, which may be fixed or moveable, as described with respect to FIG. 5. In addition to the components included in imaging system 72 (FIG. 5), imaging system 142 includes a second flat panel digital projection radiographic detector 144 that is positioned in front of flat panel detector 88 in the x-ray penetration direction 140, such that a portion of the beam of x-rays 80 emitting from x-ray source 74 pass through second flat panel detector 144 prior to impinging upon flat panel detector 88. Flat panel detectors 88, 144 may be constructed having different attenuation characteristics, according to various embodiments. For example, the scintillators of flat panel detectors 82, 144 may have different thicknesses (measured in the y-direction 146) or be made with different scintillator materials such that flat panel detector 144 absorbs lower-energy x-rays and flat panel detector 88 absorbs higher-energy x-rays. Imaging system 142 may also include a collimating assembly or grid (not shown), similar to optional collimating assembly 138 (FIG. 5), positioned in front of each flat panel detector 88, 144.

Figure 10:
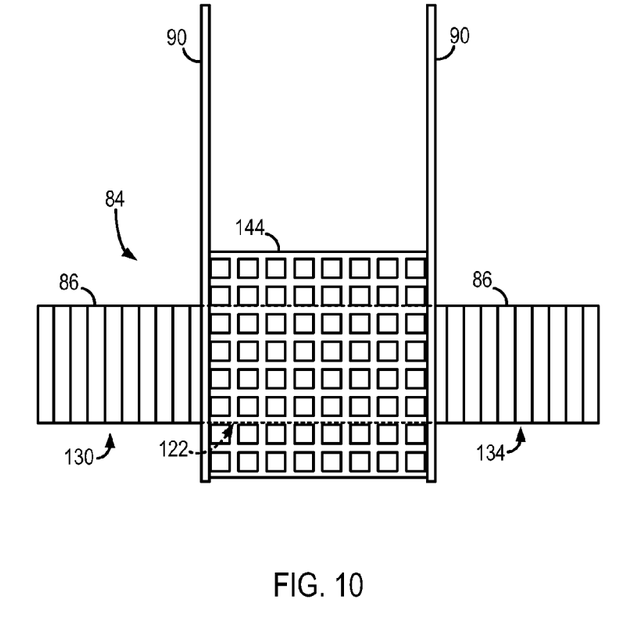
FIG. 10 is a block schematic diagram of the detector assembly of FIG. 9 illustrating a second flat panel detector in a first position.
Figure 11:
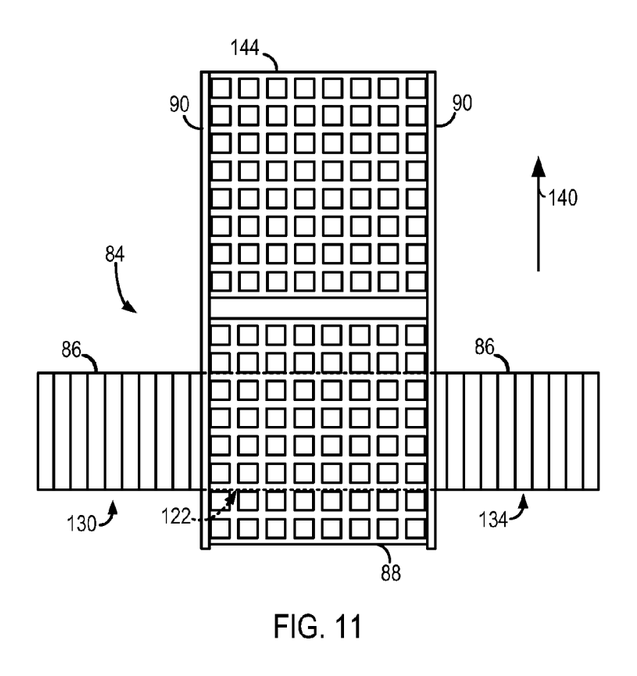
FIG. 11 is a block schematic diagram of the detector assembly of FIG. 9 illustrating a second flat panel detector in a second position.

In one embodiment, second flat panel detector 144 is slidably mounted on guide rails 148, which allow second flat panel detector 144 to be moved into and out of beam of x-rays 80, as shown in FIGS. 10 and 11. Referring first to FIG. 10, a block schematic diagram of detector assembly 84 is illustrated with second flat panel detector 144 in a first position, wherein second flat panel detector 144 is positioned above and substantially overlaps flat panel digital projection radiographic detector 88 and center portion 122 of curvilinear detector assembly 86. When second flat panel detector 144 is in this first position, a portion of x-rays 80 emitting toward flat panel detector 88 are absorbed by second flat panel detector 144, while another portion of x-rays 80 pass through second flat panel detector 144 and impinge flat panel detector 88. Since flat panel detector 88 is in front of center portion 122 of curvilinear detector assembly 86, flat panel detector 88 x-rays from impinging curvilinear detector assembly 86. FIG. 11 illustrates second flat panel detector 144 after being moved along guide rails 148 into a second position, wherein second flat panel detector 144 is offset from flat panel detector 88 in the z-direction 96. Thus, when second flat panel detector 144 is in the second position, x-rays 80 directed in the x-ray penetration direction 140 impinge flat panel detector 88 without first passing through second flat panel detector 144.

Referring again to FIG. 9, a notch filter 150 may be positioned between the first and second flat panel detectors 88, 144 in the x-ray penetration direction x-ray penetration direction 140 for use in energy discrimination computed tomography (EDCT) applications. Notch filter 150 is constructed of an x-ray attenuating material that provides for a greater energy separation band or notch between the higher energy x-rays and the lower energy x-rays in the band of x-rays 80 emitted from x-ray source 74. According to various embodiments, notch filter 150 may be constructed of a single material or a composite material to broaden the width of the notch of filtered x-rays. Further, imaging system 72 may include a number of interchangeable notch filters 150 having different filtering properties, which can be selected based on the specifications of a given scan. Notch filter 150 may be slidably mounted on guide rails 152, in a similar manner as described above with respect to second flat panel detector 144. One skilled in the art will recognize that an imaging system may include a pair of flat panel detectors, similar to detectors 88, 144, without a notch filter, according to an alternative embodiment. Further, notch filter 150 may be positioned between patient 82 and second flat panel detector 144.

By combining a flat panel detector 88 and a curvilinear detector assembly 86, the resulting detector assembly 84 leverages the benefits of both flat panel detector technology and curvilinear detector technology while mitigating the negative aspects inherent in both types of detectors. For example, because the electrical charge from all of the detector elements on a given read line of a flat panel detector is fed onto the single readout circuit for that line, the sampling speed of a flat panel detector is lower than that of conventional curvilinear detector assemblies. However, because flat panel detector 88 is positioned at the center of the field of view, flat panel detector 88 acquires attenuation data corresponding to the slowest moving portion of the image. Also, because the manufacture of a flat panel detector is more cost effective than a curvilinear detector having a similar coverage area, use of flat panel detector 84 at the center of detector assembly 84 reduces the overall cost of detector assembly 84 while allowing for increased coverage in the z-direction 94 (i.e., along the patient axis). The longer lag or afterglow inherent in the use of flat panel detectors is also mitigated when by positioning flat panel detector 84 in the center of the field of view. Finally, the limited dynamic range of a flat panel detector may be mitigated through the use of a second flat panel detector, such as second flat panel detector 144, for example. Detector assembly 84 is particularly advantageous for use in cardiac CT imaging applications, as flat panel detector 84 provides the resolution and coverage desired for cardiac imaging.

In accordance with the above-described imaging systems and methods, one skilled in the art will recognize that one or more flat panel detectors, such as flat panel detectors 88, 144, may be added to an existing conventional CT imaging system having a curvilinear detector assembly in order to retrofit the system for cardiac imaging. Such a retrofit system may include moveable guide rails, similar to guide rails 152 (FIG. 10) for example, to allow flat panel detector(s) to be moved into and out of the beam of x-rays depending on the desired scan parameters.

Figure 12:
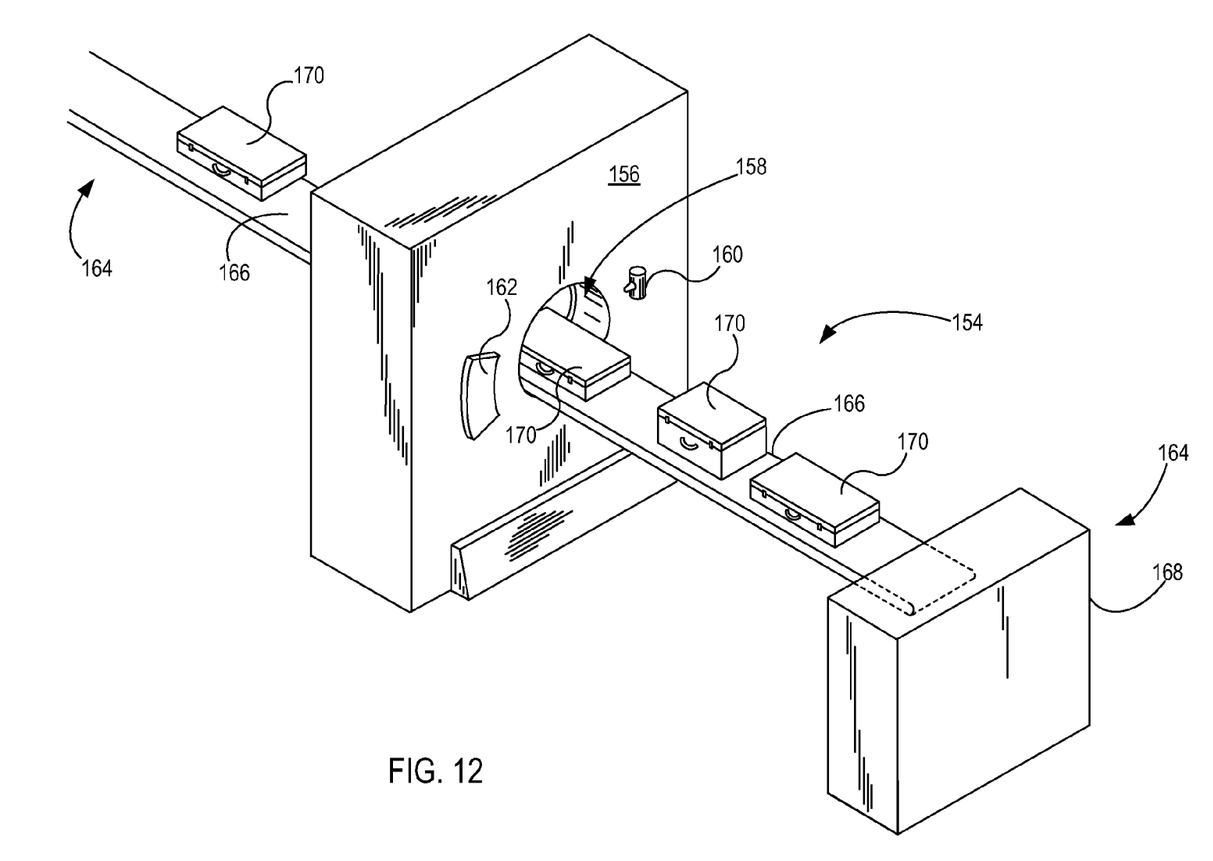
FIG. 12 is a pictorial view of a CT system for use with a non-invasive package inspection system.

Referring now to FIG. 12, package/baggage inspection system 154 includes a rotatable gantry 156 having an opening 158 therein through which packages or pieces of baggage may pass. The rotatable gantry 156 houses a high frequency electromagnetic energy source 160 as well as a detector assembly 162 having scintillator arrays comprised of scintillator cells similar to that shown in FIG. 3 or 4. A conveyor system 164 is also provided and includes a conveyor belt 166 supported by structure 168 to automatically and continuously pass packages or baggage pieces 170 through opening 158 to be scanned. Objects 170 are fed through opening 158 by conveyor belt 166, imaging data is then acquired, and the conveyor belt 166 removes the packages 170 from opening 158 in a controlled and continuous manner. As a result, postal inspectors, baggage handlers, and other security personnel may non-invasively inspect the contents of packages 170 for explosives, knives, guns, contraband, etc.

One skilled in the art will appreciate that embodiments of the invention may be interfaced to and controlled by a computer readable storage medium having stored thereon a computer program. The computer readable storage medium includes a plurality of components such as one or more of electronic components, hardware components, and/or computer software components. These components may include one or more computer readable storage media that generally stores instructions such as software, firmware and/or assembly language for performing one or more portions of one or more implementations or embodiments of a sequence. These computer readable storage media are generally non-transitory and/or tangible. Examples of such a computer readable storage medium include a recordable data storage medium of a computer and/or storage device. The computer readable storage media may employ, for example, one or more of a magnetic, electrical, optical, biological, and/or atomic data storage medium. Further, such media may take the form of, for example, floppy disks, magnetic tapes, CD-ROMs, DVD-ROMs, hard disk drives, and/or electronic memory. Other forms of non-transitory and/or tangible computer readable storage media not list may be employed with embodiments of the invention.

A number of such components can be combined or divided in an implementation of a system. Further, such components may include a set and/or series of computer instructions written in or implemented with any of a number of programming languages, as will be appreciated by those skilled in the art. In addition, other forms of computer readable media such as a carrier wave may be employed to embody a computer data signal representing a sequence of instructions that when executed by one or more computers causes the one or more computers to perform one or more portions of one or more implementations or embodiments of a sequence.

Therefore, in accordance with one embodiment, an x-ray detector assembly includes a curvilinear detector assembly that has a first side section that includes a first plurality of detector modules, a second side section that includes a second plurality of detector modules, and a third section that includes a third plurality of detector modules. The third section is positioned between the first and second side sections in a channel direction. The x-ray detector assembly also includes a first flat panel digital projection detector and a first detector mounting structure that is configured to align the first flat panel digital projection detector in a first position to block the third section of the curvilinear detector assembly from receiving x-rays emitting from an x-ray source toward the curvilinear detector assembly in the x-ray penetration direction.

In accordance with another embodiment, a method of manufacturing a detector assembly includes the step of providing a curvilinear detector array comprising a plurality of detectors arranged therein, the curvilinear detector array having a length defined in a channel direction between a first side and a second side of the curvilinear detector array and a width defined in a slice direction between a third side and a fourth side of the curvilinear detector array. The method also includes the step of providing a first flat panel detector comprising a top surface configured to face an x-ray source, the top surface having a width defined in the slice direction between a first edge of the top surface and a second edge of the top surface opposite the first edge, wherein the width of the first flat panel detector is greater than the width of the curvilinear detector array. Further, the method includes the step of coupling the first flat panel detector to a first detector mounting assembly having an obstructing position configured to align the first flat panel detector above the curvilinear detector array in an x-ray penetration direction such that the first flat panel detector is substantially aligned with a central portion of the curvilinear detector array in the slice and channel directions.

In accordance with yet another embodiment, a CT system includes a rotatable gantry having an opening therein for receiving an object to be scanned, a table positioned within the opening of the rotatable gantry and moveable through the opening in a z-direction, and an x-ray source coupled to the rotatable gantry and configured to project a beam of x-rays toward the object to be scanned. The CT system also includes a detector assembly positioned to receive the beam of x-rays from the x-ray source. The detector assembly includes a curvilinear detector assembly having a plurality of detectors and a first flat panel digital detector arranged between a central portion of the curvilinear detector assembly and the x-ray source such that a first plurality of x-rays projecting from the x-ray source toward the central portion of the curvilinear detector assembly are absorbed by the first flat panel digital detector.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An x-ray detector assembly comprising:
   a curvilinear detector assembly comprising:
      a first side section comprising a first plurality of detector modules;
      a second side section comprising a second plurality of detector modules; and
      a third section comprising a third plurality of detector modules, the third section positioned between the first and second side sections in a channel direction;
   a first flat panel digital projection detector; and
   a first detector mounting structure configured to align the first flat panel digital projection detector in a first position to block the third section of the curvilinear detector assembly from receiving x-rays emitting from an x-ray source toward the curvilinear detector assembly in the x-ray penetration direction.

2. The x-ray detector assembly of claim 1 wherein the first detector mounting structure comprises guide rails configured to allow the first flat panel digital projection detector to be moved between the first position and a second position; and
   wherein, when in the second position, the first flat panel digital projection detector is misaligned with the third section of the curvilinear detector assembly such that x-rays emitting from the x-ray source in the x-ray penetration direction impinge upon the third plurality of detector modules of the curvilinear detector assembly without passing through the first flat panel digital projection detector.

3. The x-ray detector assembly of claim 1 further comprising:
   a second flat panel digital projection detector; and
   a second detector mounting structure configured to align the second flat panel digital projection detector in a first position with the first flat panel digital projection detector and the center section of the curvilinear detector assembly such that x-rays emitting from the x-ray source and passing through the second flat panel digital projection detector in the x-ray penetration direction impinge upon the first flat panel digital projection detector.

4. The x-ray detector assembly of claim 3 wherein the second detector mounting structure comprises guide rails configured to allow the second flat panel digital projection detector to be moved between the first position and a second position; and
   wherein, when in the second position, the second flat panel digital projection detector is misaligned with the first flat panel digital projection detector such that x-rays emitting from the x-ray source in the x-ray penetration direction impinge upon the first flat panel digital projection detector without passing through the second flat panel digital projection detector.

5. The x-ray detector assembly of claim 1 further comprising a notch filter comprising an x-ray attenuating material selected to filter x-rays within a given energy band.

6. The x-ray detector assembly of claim 5 wherein the notch filter is positioned between the first flat panel digital projection detector and the second flat panel digital projection detector.

7. The x-ray detector assembly of claim 3 wherein the first flat panel digital projection detector is configured to absorb high-energy x-rays; and
wherein the second flat panel digital projection detector is configured to absorb low-energy x-rays.

8. The x-ray detector assembly of claim 1 wherein the plurality of detector modules of the curvilinear detector assembly have a width in the channel direction of approximately 16 mm; and
wherein the first flat panel digital projection detector has a width in the channel direction of approximately 20 cm.

9. A method of manufacturing a detector assembly comprising:
providing a curvilinear detector array comprising a plurality of detectors arranged therein, the curvilinear detector array having a length defined in a channel direction between a first side and a second side of the curvilinear detector array and a width defined in a slice direction between a third side and a fourth side of the curvilinear detector array;
providing a first flat panel detector comprising a top surface configured to face an x-ray source, the top surface having a width defined in the slice direction between a first edge of the top surface and a second edge of the top surface opposite the first edge, wherein the width of the first flat panel detector is greater than the width of the curvilinear detector array; and
coupling the first flat panel detector to a first detector mounting assembly having an obstructing position configured to align the first flat panel detector above the curvilinear detector array in an x-ray penetration direction such that the first flat panel detector is substantially aligned with a central portion of the curvilinear detector array in the slice and channel directions.

10. The method of claim 9 further comprising providing the first detector mounting assembly having the obstructing position and a non-obstructing position, the non-obstructing position configured to misalign the first flat panel detector with respect to the second flat panel detector such that x-rays emitting from the x-ray source in the x-ray penetration direction impinge upon the second flat panel detector without passing through the first flat panel detector.

11. The method of manufacturing of claim 9 further comprising:
providing a second flat panel detector; and
coupling the second flat panel detector to a second detector mounting assembly having an obstructing position configured to align the second flat panel detector above the first flat panel detector in an x-ray penetration direction such that x-rays emitting from an x-ray source and passing through the second flat panel detector in the x-ray penetration direction impinge upon the first flat panel detector.

12. The method of manufacturing of claim 11 further comprising providing the second mounting assembly having the obstructing position and a non-obstructing position, the non-obstructing position configured to misalign the second flat panel detector with respect to the first flat panel detector such that x-rays emitting from the x-ray source in the x-ray penetration direction impinge upon the first flat panel detector without passing through the second flat panel detector.

13. The method of manufacturing of claim 9 further comprising positioning a notch filter above the first flat panel detector in the x-ray penetration direction.

14. The method of manufacturing of claim 9 wherein providing the first flat panel detector comprises providing a digital projection radiographic detector having a coverage area at least equal in size to a complete projection of an average adult heart.

15. A computed tomography (CT) system comprising:
a rotatable gantry having an opening therein for receiving an object to be scanned;
a table positioned within the opening of the rotatable gantry and moveable through the opening in a z-direction;
an x-ray source coupled to the rotatable gantry and configured to project a beam of x-rays toward the object to be scanned; and
a detector assembly positioned to receive the beam of x-rays from the x-ray source, the detector assembly comprising:
a curvilinear detector assembly comprising a plurality of detectors; and
a first flat panel digital detector arranged between a central portion of the curvilinear detector assembly and the x-ray source such that a first plurality of x-rays projecting from the x-ray source toward the central portion of the curvilinear detector assembly are absorbed by the first flat panel digital detector.

16. The CT system of claim 15 further comprising a notch filter positioned between the first flat panel digital detector and the x-ray source.

17. The CT system of claim 15 further comprising a second flat panel digital detector positioned between the first flat panel digital detector and the x-ray source such that the first plurality of x-rays traveling in the x-ray projection direction pass through the second flat panel digital detector prior to impinging upon the first flat panel digital detector.

18. The CT system of claim 17 wherein the second flat panel digital detector has a thickness in an x-ray penetration direction that is less than a corresponding thickness of the first flat panel digital detector.

19. The CT system of claim 17 wherein the first flat panel digital detector comprises a first scintillating material configured to absorb high-energy x-rays; and
wherein the second flat panel digital detector comprises a second scintillating material configured to absorb low-energy x-rays.

20. The CT system of claim 15 wherein the first flat panel digital detector has a coverage area that is large enough to acquire projection data for a whole adult heart during one rotation of the rotatable gantry.

21. The CT system of claim 15 further comprising:
a data acquisition system configured to receive projection data from the curvilinear detector assembly and the first flat panel digital detector; and
an image reconstructor coupled to the data acquisition system to receive the projection data, wherein the processor is programmed to apply calibration and corrections to the projection data to account for interference between the curvilinear detector assembly and the first flat panel digital detector.

* * * * *